(12) United States Patent
Narula et al.

(10) Patent No.: US 7,419,943 B2
(45) Date of Patent: Sep. 2, 2008

(54) METHANOAZUENOFURANS AND METHANOAZULENONE COMPOUNDS AND USES OF THESE COMPOUNDS AS FRAGRANCE MATERIALS

(75) Inventors: Anubhav P. S. Narula, Hazlet, NJ (US); Edward Mark Arruda, Cliffwood, NJ (US); Adam Jan Janczuk, Parlin, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 873 days.

(21) Appl. No.: 10/923,393

(22) Filed: Aug. 20, 2004

(65) Prior Publication Data

US 2006/0040849 A1     Feb. 23, 2006

(51) Int. Cl.
  *C11D 3/50*  (2006.01)
  *A61K 8/00*  (2006.01)

(52) U.S. Cl. .......................... 510/103; 512/11; 512/15; 549/429; 568/373

(58) Field of Classification Search ................ None
  See application file for complete search history.

(56) References Cited

U.S. PATENT DOCUMENTS 5,892,062 A    4/1999  Pickenhagen et al.

FOREIGN PATENT DOCUMENTS

JP   2003 137758 A2   5/2003
JP   2003 192560 A2   7/2003

OTHER PUBLICATIONS

M. Aberchane et al., Acta Botanica Gallica, vol. 150, issue 2, pp. 223-229, 2003. No month available. Abstract only.*

(Continued)

Primary Examiner—John R Hardee
(74) Attorney, Agent, or Firm—Elizabeth M. Quirk; XuFan Tseng; Joseph F. Leightner

(57) ABSTRACT

The use of novel methanoazulenofuran and methanoazulenone compounds for use as fragrance chemicals, suitable for use incorporated in a wide variety of products such as perfumes, colognes and personal care products having a structure

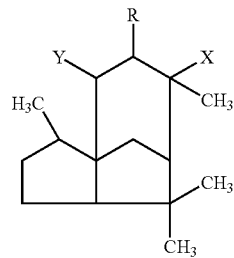

wherein R is =O, X is selected from the group consisting of H, $CH_3$, $C_2H_5$, and $CH_2CH=CH_2$;
or wherein R forms a fused ring

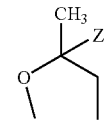

with the ring carbon at the X position, X is absent; and
Y and Z are selected from the group consisting of H and $CH_3$.

12 Claims, 2 Drawing Sheets

OTHER PUBLICATIONS

K. Ahmed et al., Pakistan Journal of Scientific and Industrial Research, vol. 44, issue 4, 2001. No month available. Abstract only.*

Y. Naves et al., Helvetica Chimica Acta, vol. 26, pp. 302-337, 1943. No month available. Abstract only.*

Ter Heide, R. et al. "On the Chemical Composition of Cedarwood Oil (Juniperus Virginians L.)" Developments in Food Science (1988, no month available), (18) 627-639.

Kasano, Masanobu, et al. "Oxidation of .alpha.-cedrene with lead tetraacetate" Nippon Kagaku Kaishi (1977, no month available), (10) 1502-1504.

* cited by examiner

METHANOAZUENOFURANS AND METHANOAZULENONE COMPOUNDS AND USES OF THESE COMPOUNDS AS FRAGRANCE MATERIALS

FIELD OF THE INVENTION

Novel methanoazuenofurans and methanoazulenone compounds are disclosed, these compositions are suitable for use as a fragrance chemical suitable for incorporation in fine fragrances, cosmetics, toiletries, personal care products, cleaning products, laundry products and related applications.

BACKGROUND OF THE INVENTION

There is an ongoing need in the fragrance and flavor industry to provide new chemicals to give perfumers and other persons ability to create new fragrances for perfumes, colognes and personal care products. Although numerous fragrance chemicals are known and commercially available, there is an ongoing and unmet need for new fragrance chemicals in order to create new fragrances with different notes and qualities.

SUMMARY OF THE INVENTION

The present invention is directed to compounds of the formula:

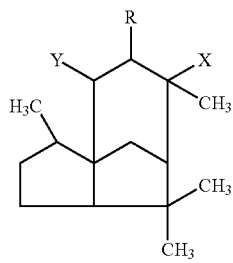

wherein R is =O, X is selected from the group consisting of H, $CH_3$, $C_2H_5$, and $CH_2CH=CH_2$;
or wherein R forms a fused ring

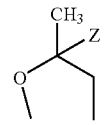

with the ring carbon at the X position, X is absent; and
Y and Z are selected from the group consisting of H and $CH_3$.

In addition, the present invention is directed to the use of the above compounds as a fragrance chemical to enhance the olfactory effect of perfumes, toilet waters, colognes, personal products and the like. More specifically, in a further embodiment the present invention is a method for enhancing a perfume by incorporating an olfactory acceptable amount of compounds of the formula set forth above.

These and other embodiments of the present invention will be apparent by reading the following specification.

DETAILED DESCRIPTION OF THE INVENTION

Figure 1:
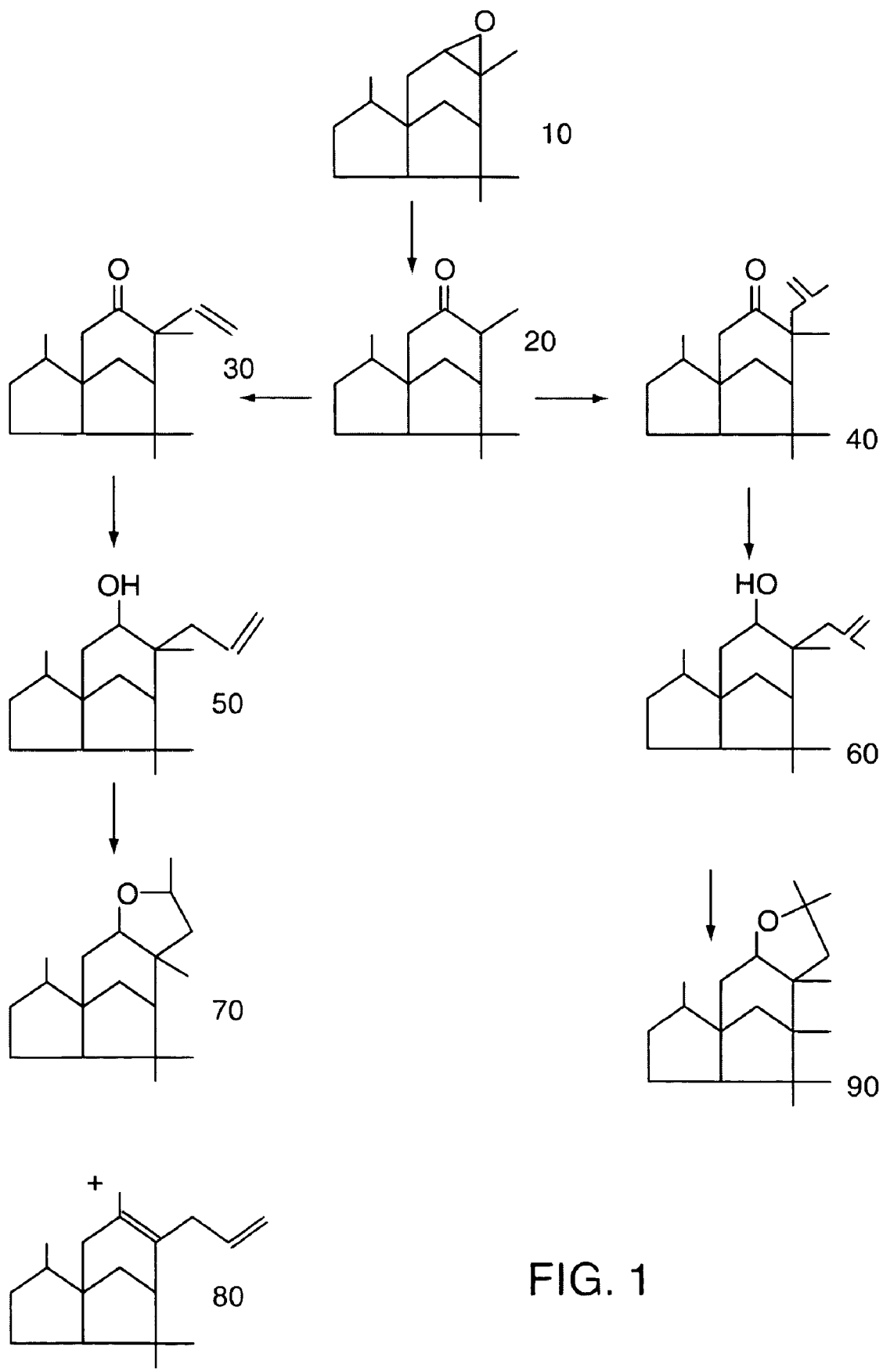
FIGS. 1 and 2 depict various routes to synthesize the various compounds of the present invention.

In one embodiment, the present invention is directed to the novel compounds described above.

In another embodiment the present invention, is directed to the use of the compounds in fragrance formulations.

The specific compounds and the olfactory characteristics of the compounds are set forth in the Table below:

TABLE

| COMPOUND | X | Y | R | ODOR NOTE |
|---|---|---|---|---|
| 2H-4,8A-Methanoazuleno[5,6,-B] Furan, Decahydro-2,2,3A,5,5,8-Hexamethyl (CD 36084) | Absent | H | Fused Ring Z=$CH_3$ | Strong, methyl encyclene |
| 1H-3A,7-Methanoazulen-5(4H)-One, Hexahydro-3,6,8,8-Tetramethyl-6-(2-Propenyl) (CD 35957) | $CH_2CH=CH_2$ | H | =O | Weak encyclene notes |
| 1H-3A,7-Methanoazulen-5(4H)-One Hexahydro-3,6,6,8,8-Pentamethyl (CD-36008) | $CH_3$ | H | =O | Soft, woody ambery |
| 1H-3A,7-Methanoazulen-5(4H)-One Hexahydro-3,4,6,8,8-Pentamethyl CD35930) | H | $CH_3$ | =O | Whitewood, soft, weak |
| 1H-3A,7-Methanoazulen-5(4H)-One, 6-Ethylhexahydro-3,6,8,8-Tetramethyl (CD36076) | $CH_2CH_3$ | H | =O | Weak amber note |
| 2H-4,8A-Methanoazuleno[5,6-B] Furan, Decahydro-2,3A,5,5,8-Pentamethyl (CD36101) | Absent | H | Fused Ring Z=H | |
| 1H-3A,7-Methanoazulen-5(4H)-One, Hexahydro-3,6,8,8-Tetramethyl-6-(2-Methyl-2-Propenyl) (CD36004) | $H_2CC(CH_3)=CH_2$ | H | =O | |

The use of these compounds are widely applicable in current perfumery products, including the preparation of perfumes and colognes, the perfuming of personal care products such as soaps, shower gels, and hair care products as well as air fresheners, candles and cosmetic products. The compound can also be used to perfume candles and cleaning agents, such as, but not limited to soaps, detergents, fabric softeners, fabric softening sheets, dishwashing materials, scrubbing compositions, window cleaners, and the like.

In these preparations, the compounds of the present invention can be used alone or in combination with other fragrance compositions, solvents, adjuvants and the like. Those with skill in the art will appreciate the nature and variety of the other ingredients that can be used in combination with the compound of the present invention.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. Nos. 4,534,891, 5,559,088, 6,086,903 and 6,680,289. Another source of suitable fragrances is found in *Perfumes, Cosmetics and Soaps,* Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein olfactory effective amount is understood to mean the amount of compound in perfume compositions the individual component will contribute to its particular olfactory characteristics, but the olfactory effect of the perfume composition will be the sum of the effects of each of the perfume or fragrance ingredients. Thus the compounds of the invention can be used to alter the aroma characteristics of the perfume composition by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.1 to about 8 and most preferably from about 0.5 to about 5 weight percent. In addition to the compounds, other agents can be used in conjunction with the fragrance. Well known materials such as surfactants, emulsifiers, and polymers to encapsulate the fragrance can also be employed without departing from the scope of the present invention.

Another method of reporting the level of the compound of the invention in the perfumed composition, i.e., the compounds as a weight percentage of the materials added to impart the desired fragrance. The compounds of the invention can range widely from 0.005 to about 10 weight percent of the perfumed composition, and preferably from about 0.1 to about 5 weight percent. Those with skill in the art will be able to employ the desired level of the compound of the invention to provide the desired fragrance and intensity.

As described herein, the present invention is well suited for use in a variety of well-known consumer products such as laundry detergents and fabric softeners, liquid dish detergents, automatic dish detergents, as well as soaps, body washes, hair shampoos and conditioners. These products employ surfactant and emulsifying systems that are well known. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, 4,767,547 and 4,424,134. Liquid dish detergents are described in U.S. Pat. Nos. 6,069,122 and 5,990,065 and automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents useful in the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoo and conditioners that can employ the present invention include U.S. Pat. Nos. 6,162,423, 5,968,286, 5,935,561, 5,932,203, 5,837, 661, 5,776,443, 5,756,436, 5,661,118, 5,618,523, 5,275,755, 5,085,857, 4,673,568, 4,387,090, and 4,705,681.

Figure 2:
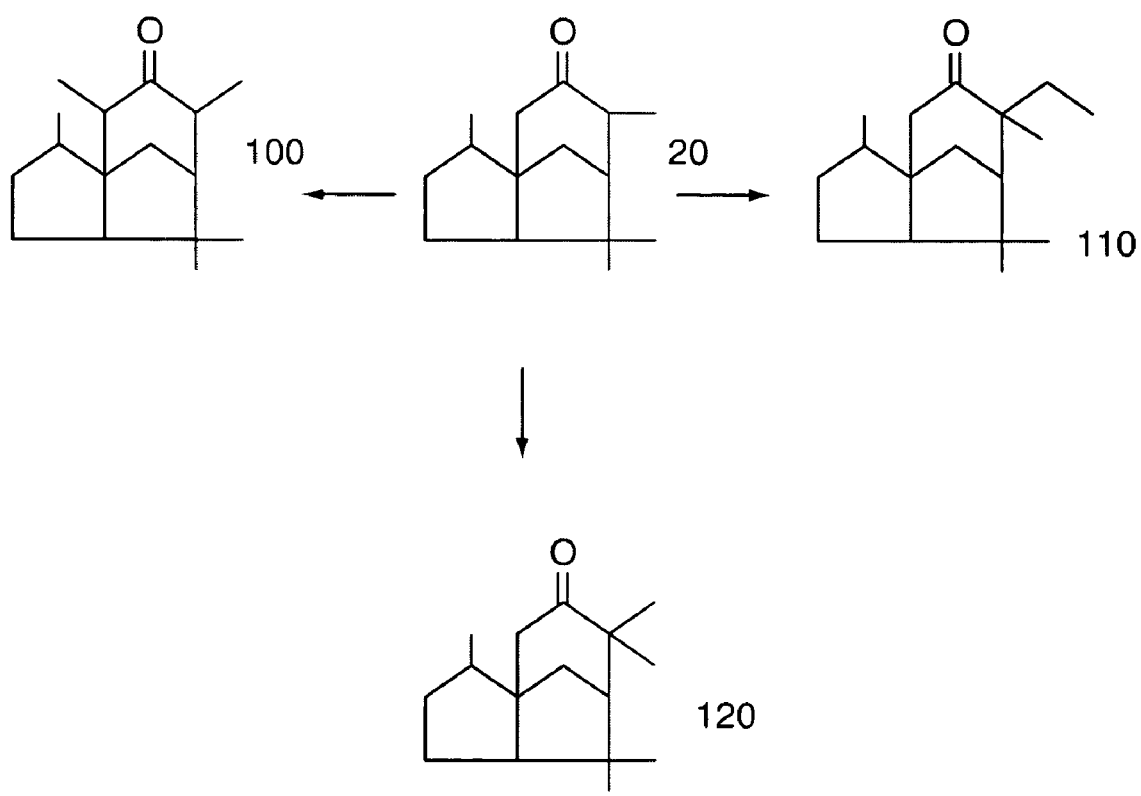

Referring to FIGS. 1 and 2 a diagram of the reaction synthesis is presented. Referring specifically to FIG. 1, the preferred starting material is Andrane (10) which when reacted with $BF_3 \cdot Et_2O$ forms Cedrone (20). After isolation and purification, Cedrone can then be reacted in the presence of NaH/ tetrahydrofuran (THF) and toluene in several different reaction sequences.

For example, when reacted with allyl chloride in the presence of NaH/THF in tolune, Cedrone forms allyl cedrone (30). The reaction product is then further reacted, in a reduction reaction, in the presence of toluene and Red-Al or Vitride (sodium bis(2-methoxyethoxy) aluminum hydride, commercially available from Aldrich )to form allyl cedrol (50). The allyl cedrol product is then further reacted with methane sulfonic acid (MSA)/toluene to form 2H-4,8A-methanoazueno[5,6-B] furan decahydro-2,3A,5,5,8-pentamethyl (70), and the by-product 2,3,4,7,8,8A-hexahydro-3,6,8,8-tetramethyl-7-prop-2-ene-1H-3A, 4-methanoazulene (80).

An alternative reaction sequence is to react Cedrone with methallyl chloride(3-chloro-2-methylpropene) in the presence of NaH/THF in toluene and a catalytic amount of NaI, to form methallyl cedrone (40). The methallyl cedrone product is then reacted further with RED-Al or Vitride to form methallyl cedrol (60). The methally cedrol product is then further reacted with MSA/toluene to form 2H,4,8A-methanoazueno [5,6-B] furan decahydro-2,2,3a,5,5,8-hexamethyl (90).

Referring to FIG. 2, a third reaction sequence is the reaction of cedrone with a catalytic amount of $CH_3I$ in the presence NaH/THF toluene provides alpha-methyl cedrone (120).

Another reaction can be conducted with cedrone which is then reacted with methyl-Lithium/diethyl ether to form alpha-methyl methylcedrol (100).

A further reaction product is provided by the reaction of Cedrone with ethyl iodide in the presence of NaH/THF and toluene to form alpha-ethyl cedrone (110).

All U.S. patents and patent applications referenced in this application are hereby incorporated by reference as if set forth by their entirety.

The following examples are provided as specific embodiments of the present invention. Other modifications of this invention will be readily apparent to those skilled in the art, without departing from the scope of this invention. As used herein, both specification and following examples all percentages are weight percent unless noted to the contrary. IFF as used in the examples is understood to mean International Flavors & Fragrances Inc., DPG is understood to mean dipropylene glycol, DEP is understood to mean diethyl phthalate.

EXAMPLE 1

Preparation of Cedrone

1683 Grams of ANDRANE (alpha-epoxy-cedrene, commercially available from IFF) and 800 grams of toluene were charged to a 5 liter reaction flask at room temperature. 5.4 Grams of $BF_3$.etherate complex was added drop wise while maintaining at room temperature. After all of the $BF_3$ etherate has been added, the contents of the flask were gradually allowed to warm. Flask temperature was maintained at less than about 50° C. reaction temperature until the reaction was substantially cooled and the reaction terminated.

The reaction contents were quenched with two water washes, one $NaHCO_3$ wash and a brine wash.

The yield was 1609.3 grams of product which is a 95.6% yield.

EXAMPLE 2

PREPARATION OF 1H-3A,7-METHANAOAZU-LEN-5(4H)-ONE, HEXAHYDRO-3,6,8,8-TET-RAMETHYL-6-(2-PROPENYL)

The following materials were charged to a 2 liter reaction flask and warmed to 60° C.:
44 grams of 60% NaH;
200 grams of tetrahydofuran (THF)
50 grams of toluene; and
150 grams of NaI.

Over one hour, 200 grams of Cedrone (IFF) was added to the reaction flask at 70° C. Then over a two hour period, 92 grams of allyl chloride was added to the reaction flask at 65° C. and the contents were allowed to age for several hours. The contents were then cooled.

The reaction contents were quenched with methanol, washed twice with water and once with brine.

GLC indicated an 88% product purity.

165 Grams of product was recovered for a 63.5% yield.

The nmr spectrum of the product was: 0.88-1.08 ppm(ms, 12H), 1.25 ppm(s,1H), 1.3-1.42ppm(bm, 3H, 1.6 ppm (s,2H), 1.68-2.5 ppm(m,9H), 2.6 ppm(d,1H), 5.1 ppm(m,2H), 5.7 ppm(m,1H).

EXAMPLE 3

PREPARATION OF 1H,3A-7-METHANOAZU-LEN-5(4H)-ONE, HEXAHYDRO-3,6,8,8-TET-RAMETHYL-6-(2-methyl-2-PROPENYL)

The following materials were charged to a 2 liter reaction flask at room temperature and then heated to 65° C.:
88 grams of NaH (60%);
400 grams of THF;
100 grams of toluene; and
7.5 grams of NaI.

Over about two hours, 440 grams of CEDRONE was added to the flask at 65° C. Then 217 grams of 3-chloro-2-methylpropene was added over about 90 minutes. The contents were allowed to age at 75° C. for 3.5 hours.

The reaction contents were allowed to cool and a GLC was run when the reaction was complete. The product was washed with methanol, two water washes and a brine wash. The GLC indicates 83.3% product crude, 342.9 isolated product produced and 175.8 grams of refined product.

The nmr spectrum of the product was: 0.88-1.25 ppm(ms, 12H), 1.25 ppm(s,1H), 1.65 ppm (s,3H), 1.3-1.9 ppm(m,8H), 2.2 ppm(d,2H), 2.3 ppm(d,1H), 2.45 ppm(d,1H), 2.7 ppm(d, 1H), 4.65 ppm(s,1H), 4.8 ppm(s,1H).

EXAMPLE 4

PREPARATION OF 1H-3A,7-METHANOAZULEN-5(4H)-ONE, HEXAHYDRO-3,6,6,8,8-PENTAMETHYL

To a 2 liter reaction flask the following materials were charged and then heated to 60° C.:

| | |
|---|---|
| NaH (60% in oil) | 48 grams |
| THF | 200 grams |
| Toluene | 100 grams |

Cedrone (220 grams) were slowly charged over a two hour period to the flask. After the addition was complete, the contents were held at one hour for 60 minutes.

Methyl iodide (200 grams) was then fed into the reactor over a two hour period at 68° C. When the addition was complete, the contents were cooled to room temperature.

The reactor was then quenched with methanol, diluted with a toluene wash, then washed twice with water and one with brine. The product was purified using fractional distillation.

Approximately 204 grams of product was recovered, approximately an 87% yield with a greater than 88% purity. The nmr spectrum was: 0.87-1.25 ppm(ms,15H), 1.3-1.88 ppm(m,9H), 2.1 ppm(d,1H), 2.2 ppm(d,1H ),2.68 ppm(d, 1H).

EXAMPLE 5

PREPARATION OF 1H-3A,7-METHYLOAZULEN-5 (4H)-ONE, 6-ETHYLHEXAHYDRO-3,6,8,8-TETRAM-ETHYL

THF (200 grams) and toluene (100 grams) were charged to a two liter flask that was purged with nitrogen gas. Sodium hydride (48 grams of 60% by weight in oil) was added and the contents warmed to 65° C. Cedrone (220 grams) was added over an hour and after all of the material was added, the contents were allowed to age for one hour at 60° C. Ethyl iodine (185 grams) was added over an hour period. The contents were allowed to react at 70° C. for about 4 hours.

The contents were then cooled, quenched with methanol, diluted with toluene, washed twice with water and once with brine. The product was purified by fractional distillation. Crude GLC analysis indicated 57% product, 86% yield having greater than 90% purity.

The nmr spectrum of the product was: 0.85-1.2 ppm(ms, 15H), 1.3-1.9 ppm(m,10H), 2.08 ppm(d,1H), 2.15 ppm(d, 1H), 2.7 ppm(d,1H).

EXAMPLE 6

PREPARATION OF 2H-4,8A-METHANOAZUENO[5,6-B]FURAN DECAHYDRO-2,3A,5,5,8-PENTAMETHYL

Red-Al (sodium bis(2-methoxyethoxy)aluminium hydride from Aldrich) 65% in toluene, 172 grams in total was charged to a two liter reaction flask. Allyl cedrone 400 grams was added to the flask while maintaining the temperature below 40° C. over a period of 90 minutes. The contents were maintained at a temperature of 35° C. for about 3 hours. The flask was then cooled to 20° C.

The product was washed with EtOAc, followed by 25% sodium hydroxide and then water until the pH of the product was about 8. A first wash was done with brine. The precipitate was removed from the solvent and water and about 400 grams of crude was obtained.

The allyl cedrol product obtained above (404 grams) was charged with toluene to a reaction flask. Methane sulfonic acid (16.4 grams) was charged at 40° C. The contents were allowed to react for about one hour and then the product was cooled down.

The resulting product was quenched with 0.18 moles of NaOMe, washed twice with water and once with brine.

Fractional distillation of the product recovered 272.2 grams of product, having a purity of 80%.

The nmr spectrum of the product was: 0.85 ppm(d,3H), 1-1.3 ppm(ms,12H), 1.4-1.95(m,12H), 3.8 ppm(m,1H), 4.26 ppm(M,1H).

EXAMPLE 7

PREPARATION OF 2H,4,8A-METHANOAZUENO[5,6-B]FURAN DECAHYDRO-2,2,3a,5,5,8-HEXAMETHYL

Red-Al, 305 grams, and 200 grams of toluene were charged to a two liter reaction vessel flushed with nitrogen. Methallyl cedrone made in Example 3 above, was added to the flask over a period of 90 minutes while maintaining a reaction temperature of about 80° C. A total of 478 grams of methallyl cedrone was added. The contents of the flask was maintained at 40° C. for about 4 hours and then cooled to room temperature.

The product was quenched with 50 grams of EtOAc, washed with 25% NaOH, water washed until the pH was about 8 and washed again with brine. The methallyl cedrol product was purified by removing solvent. About 480 grams of crude product was obtained.

The product recovered above and toluene were charged to a two liter reaction flask. Methane sulfonic acid (21 grams) was charged to the reaction flask over 30 minutes. The contents of the reaction flask was then heated to 80° C. and maintained at that temperature for 4.5 hours until the reaction was complete. The contents were cooled to room temperature.

The product was quenched 0.24 moles of NaOMe, washed with water twice and once with brine. The product was purified using fractional distillation. A total of 352 grams of product was removed having a yield of 88%.

The nmr spectrum of the product was: 0.8 ppm(d,3H), 1-1.38 ppm(ms,12H), 1.25-1.88(m,12H), 2.2 ppm(d,1H), 3.96 ppm (M,1H).

EXAMPLE 8

A fragrance was prepared according to the following formulation:

| MATERIALS | PARTS |
| --- | --- |
| Material made in Example 2 | 1 |
| BORNAFIX ® (IFF) | 3 |
| CEDRAFIX ® (IFF) | 2.5 |
| CELESTOLIDE ® (IFF) | 4 |
| CITRALVA ® (IFF) | 1 |
| Citrus oil distilled | 12 |
| CYCLACET ® (IFF) | 3 |
| CYCLOGALBANIFF ® (IFF) | 1 |
| Dihydro Myrcenol | 40 |
| FLEURANIL ® (IFF) | 1 |
| Geranium Bourbon Oliffac | 0.5 |
| Hexyl Cinnamic Aldehyde | 4.5 |
| ISO E SUPER ® (IFF) | 2.5 |
| KHARISMAL ® (IFF) | 2 |
| KOAVONE ® (IFF) | 1.5 |
| Linalyl Acetate | 5 |
| PHENOXANOL ® (IFF) | 3 |
| PRECYCLEMONE B ® (IFF) | 1.5 |
| Pseudo Linalyl Acetate | 5 |
| Styralyl Acetate | 1 |
| VIGOFLOR ® | 1 |
| ZENOLIDE ® (IFF) | 4 |

This fragrance was described as having a citrus odor.

What is claimed is:

1. A method for improving, enhancing or modifying a fragrance through the addition of an olfactory acceptable amount of a compound of the formula

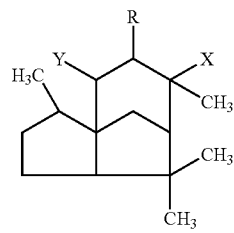

wherein R is =O,
X is selected from the group consisting of H, $CH_3$, $C_2H_5$, and $CH_2CH=CH_2$;
or wherein R forms a fused ring

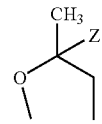

with the ring carbon at the X position, X is absent; and
Y and Z is independently selected from the group consisting of H and $CH_3$,
with the proviso that X and Y are not both H.

2. The method of claim 1, wherein the fragrance is incorporated into a product selected from the group consisting of a perfume, a cologne, a candle, a toilet water, a cosmetic product, a personal care product, a fabric care product, a cleaning product, and an air freshener.

3. The method of claim 2, wherein the cleaning product is selected from the group consisting of a soap, a detergent, a dishwashing composition, a scrubbing compound, and a window cleaner.

4. The method of claim 2, wherein the product is the personal care product.

5. The method of claim 1, wherein the amount is from about 0.005 to about 10 weight percent.

6. The method of claim 1, wherein the amount is from about 0.1 to about 8 weight percent.

7. The method of claim 1, wherein the amount is from about 0.5 to about 5 weight percent.

8. A compound of the formula

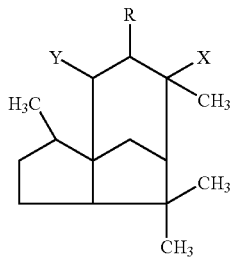

wherein R is =O,

X is selected from the group consisting of H, CH$_3$, C$_2$H$_5$, and CH$_2$CH=CH$_2$;

or wherein R forms a fused ring

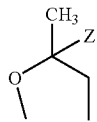

with the ring carbon at the X position, X is absent; and

Y and Z is independently selected from the group consisting of H and CH$_3$, with the proviso that X and Y are not both H.

9. The compound of claim 8 selected from the group consisting of 1H-3A,7-methanoazulen-5(4H)-one, hexahydro-3,6,8,8-tetramethyl-6-(2-Propenyl), 1H-3A,7-methanoazulen-5(4H)-one hexahydro-3,6,6,8,8-pentamethyl, 1H-3A,7-methanoazulen-5(4H)-one hexahydro-3,4,6,8,8-pentamethyl, 1H-3A,7-methanoazulen-5(4H)-one, 6-ethylhexahydro-3,6,8,8-tetramethyl and 1H-3A,7-methanoazulen-5(4H)-one, hexahydro-3,6,8,8-tetramethyl-6-(2-methyl-2-propenyl).

10. The compound of claim 8 selected from the group consisting of 2H-4,8A-methanoazuleno-[5,6,-B] furan, decahydro-2,2,3A,5,5,8-hexamethyl and 2H-4,8A-methanoazuleno-[5,6-B] furan, decahydro-2,3A,5,5,8-pentamethyl.

11. A fragrance composition containing an olfactory effective amount of the compound of claim 8.

12. A personal care product containing an olfactory effective amount of the compound of claim 8.

* * * * *